(12) United States Patent
Enderle et al.

(10) Patent No.: US 7,186,798 B2
(45) Date of Patent: Mar. 6, 2007

(54) FLUORESCENTLY LABELED GROWTH HORMONE SECRETAGOGUE

(75) Inventors: Thilo Enderle, Rheinfelden (DE); Martin Graf, Zeiningen (CH); Cornelia Hertel, Muenchenstein (CH); Sannah Jensen Zoffmann, Basel (CH); Eric Argirios Kitas, Aesch (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 85 days.

(21) Appl. No.: 11/299,533

(22) Filed: Dec. 12, 2005

(65) Prior Publication Data

US 2006/0073522 A1    Apr. 6, 2006

Related U.S. Application Data

(62) Division of application No. 10/964,878, filed on Oct. 14, 2004.

(30) Foreign Application Priority Data

Oct. 16, 2003    (EP) .................................. 03023568

(51) Int. Cl.
*A61K 38/00*    (2006.01)

(52) U.S. Cl. ...................................................... 530/324

(58) Field of Classification Search ...................... 514/2
See application file for complete search history.

(56) References Cited

FOREIGN PATENT DOCUMENTS

WO    WO 01/38355 A2    5/2001
WO    WO 01/92292 A2    12/2001

OTHER PUBLICATIONS

Codd et al, Neuropharmacol 989, 28, 1139.
Sethunadhauan et al, Biochem. Biophys. Res. Comm. 178, 31 (1991).
Bullok Kristin E. et al., Bioconjugate Chem., vol. 13, No. 6, pp. 1226-1237 (2002), XP002315750.
Lichter T. et al., FEBS Letters, vol. 431, No. 3, pp. 419-422 (1998), XP004258169.
Blackman M. J. et al., Biochemistry, vol. 41, pp. 12244-12252 (2002), XP002239039.
Muccioli G. et al., Journal of Clinical Investigation, vol. 24, pp. RC7-RC9 (2001)XP002277339.

*Primary Examiner*—Cecilia J. Tsang
*Assistant Examiner*—Maury Audet
(74) *Attorney, Agent, or Firm*—George W. Johnston; Patricia S. Rocha-Tramaloni

(57) ABSTRACT

The present invention relates to a fluorescently labeled growth hormone secretagogue which can be used for the identification of compounds capable of binding to growth hormone secretagogue receptors, in particular by high throughput screening.

5 Claims, 4 Drawing Sheets

Figure 1
Layout – 40µl assay volume /384-Well

|   | 1 | 2 | 3 | 4 | 5 | 6 | ... | 22 | 23 | 24 |
|---|---|---|---|---|---|---|---|---|---|---|
| A | FPBLK | FPBLK | S | S | S | S | S | S | S | S |
| B | FPBLK | FPBLK | S | S | S | S | S | S | S | S |
| C | FPBLK | FPBLK | S | S | S | S | S | S | S | S |
| D | FPBLK | FPBLK | S | S | S | S | S | S | S | S |
| E | 0%CTRL | 0%CTRL | S | S | S | S | S | S | S | S |
| F | 0%CTRL | 0%CTRL | S | S | S | S | S | S | S | S |
| G | 0%CTRL | 0%CTRL | S | S | S | S | S | S | S | S |
| H | 0%CTRL | 0%CTRL | S | S | S | S | S | S | S | S |
| I | 100% CTRL | 100% CTRL | S | S | S | S | S | S | S | S |
| J | 100% CTRL | 100% CTRL | S | S | S | S | S | S | S | S |
| K | 100% CTRL | 100% CTRL | S | S | S | S | S | S | S | S |
| L | 100% CTRL | 100% CTRL | S | S | S | S | S | S | S | S |
| M | STD | STD | S | S | S | S | S | S | S | S |
| N | STD | STD | S | S | S | S | S | S | S | S |
| O | STD | STD | S | S | S | S | S | S | S | S |
| P | STD | STD | S | S | S | S | S | S | S | S |

| Ligand | Ki | stdev | N |
|---|---|---|---|
| ghrelin(1-19)BoFl | 0.144 nM | 0.014 nM | 3 |
| ghrelin(1-19)TMR | 0.216 nM | 0.025 nM | 2 |
| ghrelin(1-19)TxR | 0.202 nM | 0.010 nM | 2 |
| ghrelin(1-19)MR121 | 0.342 nM | 0.045 nM | 4 |

SEQUENCE LISTING

```
<160> NUMBER OF SEQ ID NOS: 2

<210> SEQ ID NO 1
<211> LENGTH: 117
<212> TYPE: PRT
<213> ORGANISM: Homo sapiens
<220> FEATURE:
<221> NAME/KEY: ghrelin precursor
<222> LOCATION: (1)..(117)
<220> FEATURE:
<221> NAME/KEY: ghrelin
<222> LOCATION: (24)..(117)
<223> OTHER INFORMATION: mature protein
<220> FEATURE:
<221> NAME/KEY: ghrelin
<222> LOCATION: (26)..(26)
<223> OTHER INFORMATION: octanoyl derivative residue

<400> SEQUENCE: 1

Met Pro Ser Pro Gly Thr Val Cys Ser Leu Leu Leu Leu Gly Met Leu
1               5                   10                  15

Trp Leu Asp Leu Ala Met Ala Gly Ser Ser Phe Leu Ser Pro Glu His
            20                  25                  30

Gln Arg Val Gln Gln Arg Lys Glu Ser Lys Lys Pro Pro Ala Lys Leu
        35                  40                  45

Gln Pro Arg Ala Leu Ala Gly Trp Leu Arg Pro Glu Asp Gly Gly Gln
    50                  55                  60

Ala Glu Gly Ala Glu Asp Glu Leu Glu Val Arg Phe Asn Ala Pro Phe
```

```
                        65                  70                  75                  80
Asp Val Gly Ile Lys Leu Ser Gly Val Gln Tyr Gln Gln His Ser Gln
                        85                  90                  95
Ala Leu Gly Lys Phe Leu Gln Asp Ile Leu Trp Glu Glu Ala Lys Glu
                    100                 105                 110
Ala Pro Ala Asp Lys
            115

<210> SEQ ID NO 2
<211> LENGTH: 18
<212> TYPE: PRT
<213> ORGANISM: Homo sapiens
<220> FEATURE:
<221> NAME/KEY: ghrelin(1-19)
<222> LOCATION: (1)..(18)
<220> FEATURE:
<221> NAME/KEY: ghrelin(1-19)
<222> LOCATION: (3)..(3)
<223> OTHER INFORMATION: octanoyl derivative

<400> SEQUENCE: 2

Gly Ser Ser Phe Leu Ser Pro Glu His Gln Arg Val Gln Gln Arg Lys
1               5                   10                  15

Glu Ser
```

FLUORESCENTLY LABELED GROWTH HORMONE SECRETAGOGUE

PRIORITY TO RELATED APPLICATIONS

This application is a division of U.S. application Ser. No. 10/964,878, filed Oct. 14, 2004 now allowed; which claims the benefit of European Application No. 03023568.3, filed Oct. 16, 2003. The entire contents of the above-identified applications are hereby incorporated by reference.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Methodology is known in the art to determine the activity of a compound as a growth hormone secretagogue. For example, an ex vivo assay is described by Smith, et al., *Science*, 260, 1640–1643 (1993) (see text of FIG. 2 therein), but this assay requires the use of cell cultures and does not give an indication of competitive binding activity. Accordingly, it would be desirable to develop a non-radioactively labeled ligand which can be used to identify and characterize cellular receptors which play a role in the activity of growth hormone secretagogue. It would also be desirable to have a non-radioactively labeled ligand available for use in an assay for testing compounds for growth hormone secretagogue activity.

Such studies normally require a high specific activity radio-ligand. Previous attempts to develop a binding assay using [T]-labeled or [125I]-labeled peptide ligands derived from GHRP-6 met with limited success. See R. F. Walker, et al. *Neuropharmacol.* 989, 28, 1139 and C. Y. Bowers et al., *Biochem. Biophys. Res. Comm.* 1991, 178,31 (both of which, to the extent necessary, are herein incorporated by reference). Generally, the binding of such peptide ligands was of low affinity and of excessively high capacity. Moreover, the binding affinities did not correlate with the growth hormone secretory activity of the peptides. The lack of correlation of binding and growth hormone secretory activity most likely was the result of the relatively low specific activity (in the case of [T] GHRP-6) and non-specific binding properties of the radio-ligands.

These problems are solved by the present invention, which provides a fluorescent labeled ghrelin analog (labeled growth hormone secretagogue) which can be used in high throughput screening to identify and characterize cellular receptors which play a role in the activity of growth hormone secretagogue and for use in an assay for testing compounds for growth hormone secretagogue activity.

SUMMARY OF THE INVENTION

The present invention pertains to a labeled growth hormone secretagogue of the formula:

R1-Cys-F wherein R1 is a peptide sequence derived from the ghrelin polypeptide sequence SEQ ID NO: 1), and F is a fluorescent dye. In a preferred embodiment, R1 is SEQ ID NO: 2. In another preferred embodiment, R1 is octanoylated. In another preferred embodiment, R1 is N-octanoylated. In a more preferred embodiment, R1 is $^1$Gly-Ser-Dapa(N-octanoyl)-Phe-$^5$Leu-Ser-Pro-Glu-His-$^{10}$Gln-Arg-Val-Gln-Gln-$^{15}$Arg-Lys-Glu-Ser (SEQ ID NO: 2, wherein the serine at residue 3 has been replaced by the uncommon amino acid Dapa(N-octanoyl)) or in other words, the serine at residue 3 is substituted with the uncommon amino acid Dapa(N-octanoyl). N-octanoylation increases stability of ghrelin towards esterase activity. In an even more preferred embodiment, F is selected from the group consisting of Texas Red, Tetramethyl rhodamine, MR121. (*"New fluorescent dyes in the red region for biodiagnostics"* M. Sauer et al 1995 *J. Fluoresc.* Vol. 5, pp 247–261, or BODIPY-FL 4,4-difluoro-5,7-dimethyl-4-bora-3a,4a-diaza-s-indacene-3-propionic acid). In a most preferred embodiment, F is MR121.

The labeled growth hormone secretagogue herein described can be used for identifying a compound that can bind to a growth hormone secretagogue receptor. Said labeled growth hormone secretagogue can also be used to identify a cellular receptor as a growth hormone secretagogue receptor.

BRIEF DESCRIPTION OF THE FIGURES

FIG. 1: Set-up of HTS assay plate

Figure 2:
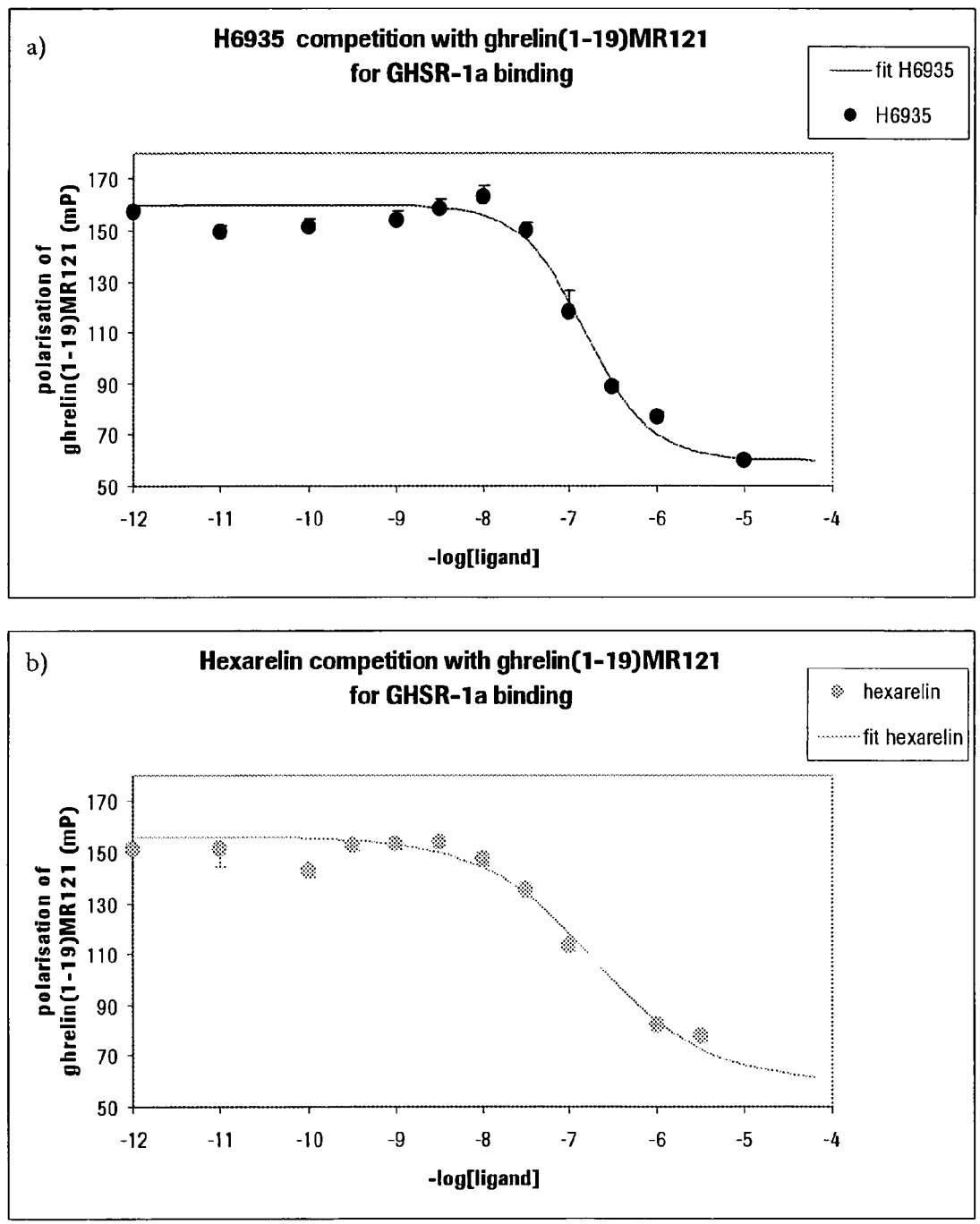
FIG. 2: Competition curves from Zeiss-System, HTS conditions. A) Competition of ghrelin (1–19) MR121 with H6935; b) Competition of ghrelin (1–19) MR121 with hexarelin.
Figure 3:
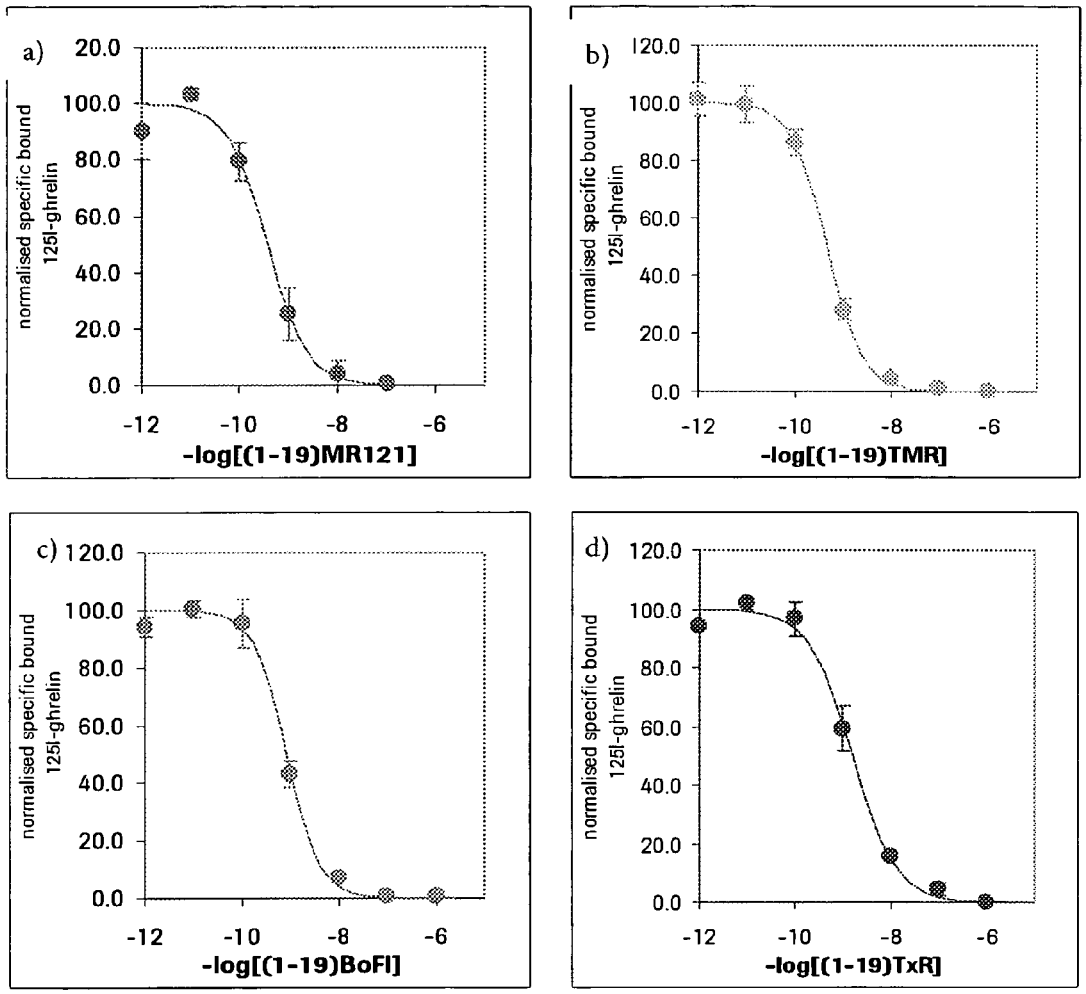
FIG. 3: Affinity of fluorescent analogs, determined in 125I-ghrelin competition assays. A) ghrelin (1–19) MR121; b) ghrelin (1–19) TMR; c) ghrelin (1–19) BoFl (BIODIPY-FL); d) ghrelin (1–19) Texas Red.
Figure 4:
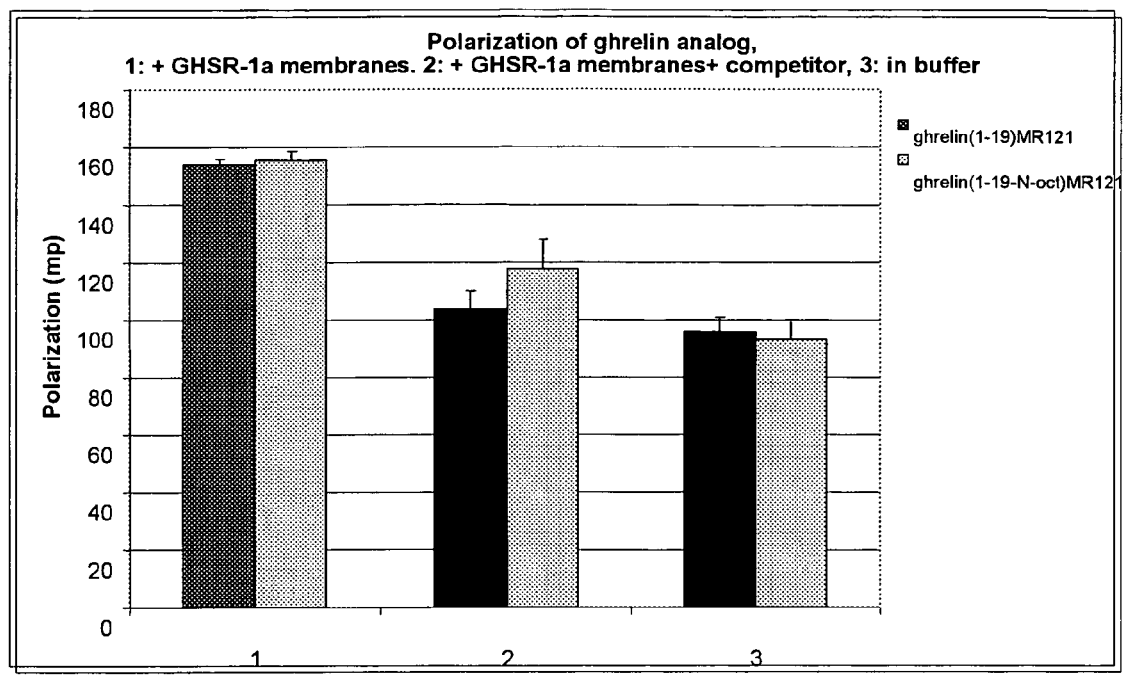
FIG. 4: Polarization of fluorescent analogs, determined according to protocol in example 2.2.1 and 2.2.2.

Red (Darker, left hand bar): ghrelin (1–19) MR121, Blue (Lighter, right hand bar): ghrelin (1–19-N-oct)MR121.

Fluorescence polarization of Total bound fluorescent ligands (in presence of GHSR-1a membranes); 2) Fluorescence polarization of Free ligand (in presence of GHSR-1a membranes and excess of competitor); 3) Fluorescence polarization of fluorescent ligands in buffer.

DETAILED DESCRIPTION OF THE INVENTION

The present invention pertains to a labeled growth hormone secretagogue of the formula:

R1-Cys-F wherein R1 is a peptide sequence derived from the ghrelin polypeptide sequence SEQ ID NO: 1), and F is a fluorescent dye. In a preferred embodiment, R1 is SEQ ID NO: 2. In another preferred embodiment, R1 is octanoylated. In another preferred embodiment, R1 is N-octanoylated. In a more preferred embodiment, R1 is $^1$Gly-Ser-Dapa(N-octanoyl)-Phe-$^5$Leu-Ser-Pro-Glu-His-$^{10}$Gln-Arg-Val-Gln-Gln-$^{15}$Arg-Lys-Glu-Ser (SEQ ID NO: 2, wherein the serine at residue 3 is substituted with Dapa(N-octanoyl)) or in other words, the serine at residue 3 is substituted with the uncommon amino acid Dapa(N-octanoyl). N-octanoylation increases stability of ghrelin towards esterase activity. In an even more preferred embodiment, F is selected from the group consisting of Texas Red, Tetramethyl rhodamine, MR121. ("*New fluorescent dyes in the red region for biodiagnostics*" M. Sauer et al 1995 *J. Fluoresc.* Vol. 5, pp 247–261, or BODIPY-FL 4,4-difluoro-5,7-dimethyl-4-bora-3a,4a-diaza-s-indacene-3-propionic acid). In a most preferred embodiment, F is MR121.

The present invention also provides a process of synthesizing a labeled ghrelin which comprises the steps of a) coupling a Cys to the C-terminal amino acid of ghrelin; and b) reacting the thiol-containing ghrelin to a fluorescent dye. Preferably, said fluorescent dye is selected from the group consisting of Texas Red, Tetramethyl rhodamine, MR121. ("*New fluorescent dyes in the red region for biodiagnostics*" M. Sauer et al 1995 *J. Fluoresc.* Vol. 5, pp 247–261, or BODIPY-FL (4,4-difluoro-5,7-dimethyl-4-bora-3a,4a-diaza-s-indacene-3-propionic acid).

The present invention also pertains to a method for identifying a compound that can bind to a growth hormone secretagogue receptor comprising contacting said compound (a "test" compound) with a host expressing a growth hormone secretagogue receptor in the presence of the labeled growth hormone secretagogue hereinbefore described, or with a membrane preparation from such a host, and monitoring whether the compound influences the binding of the labeled growth hormone secretagogue hereinbefore described to the growth hormone secretagogue receptor by measuring the fluorescence of the label of the bound labeled growth hormone secretagogue hereinbefore described.

The host may be a tissue sample, primary cells or cultured cells which either naturally expresses a growth hormone secretagogue receptor, or which are either transiently or stably transfected with a growth hormone secretagogue receptor. Methods of transfecting cells are well known in the art (Sambrook et al., Molecular Cloning: A Laboratory Manual (1989), Cold Spring Harbor Laboratory Press, New York, USA).

Preferably, said method is a high throughput screening method. The method hereinbefore described is sensitive with regard to the pH of the assay buffer used. A pH deviation of 0.2 results in a 50% loss of binding. Therefore, in a preferred embodiment, the assay buffer used in said method has a pH of 7.2. The peptides of this invention tend to absorb to surfaces. Thus, in a preferred embodiment of this invention, the plastic ware either comprises a nonbinding surface or is blocked with a casein solution. The term "plastic ware" as used herein refers to plates used for the assay, as well as any type of tube used to prepare solutions comprising the peptides of this invention. Preferably, said casein solution comprises 1% casein. More preferably, blocking is performed over night. In a most preferred embodiment, the blocked plates are washed with buffer before use.

The present invention also provides a method of identifying a cellular receptor as a growth hormone secretagogue receptor comprising contacting a host suspected to express a growth hormone secretagogue receptor with the labeled growth hormone secretagogue hereinbefore described and determining whether binding has occurred.

Furthermore, the present invention pertains to a method for identifying the activity of a compound ("test compound") as a growth hormone secretagogue comprising contacting the compound suspected of having activity as a growth hormone secretagogue with a host expressing a growth hormone secretagogue receptor in the presence of the labeled growth hormone secretagogue hereinbefore described and monitoring whether the compound suspected of having activity as a growth hormone secretagogue influences the binding of the labeled growth hormone secretagogue hereinbefore described to the growth hormone secretagogue receptor.

The present invention also provides a compound identified by methods hereinbefore described or pharmaceutically acceptable salts thereof. In addition, the present invention provides a pharmaceutical composition comprising a compound hereinbefore described and a pharmaceutically acceptable carrier.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the identified agents wherein the parent agent is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmoic, maleic, hydroxymaleic, phenylacetic, glutamic, benzoic, salicylic, sulfanilic, 2-acetoxybenzoic, fumaric, benzenesulfonic, toluenesulfonic, methanesulfonic, ethane disulfonic, oxalic, isethionic, and the like.

The term "secretagogue" means a substance that stimulates the secretion of a hormone, specifically growth hormone.

The pharmaceutically acceptable salts of the present invention can be synthesized from the parent agent which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

The agents identified by the method of the invention may be modified to achieve (i) modified site of action, spectrum of activity, and/or (ii) improved potency, and/or (iii) decreased toxicity (improved therapeutic index), and/or (iv) decreased side effects, and/or (v) modified onset of action, duration of effect, and/or (vi) modified kinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carbon acids, or (iii) esterification of hydroxyl groups to, e.g. phosphates, pyrophosphates or sulfates or hemi succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetates, or (xiv) N-acetylation to amides, phenylcarbamates, or (xv) synthesis of Mannich bases, imines, or (xvi) transformation of ketones or aldehydes to Schiff's bases, oximes, acetates, ketales, enolesters, oxazolidines, thiozolidines or combinations thereof; and (b) formulating the product of said modification with a pharmaceutically acceptable carrier or a carrier/diluent acceptable for fragrance or flavor compositions or products.

Any conventional carrier material can be utilized. The carrier material can be an organic or inorganic one suitable for eteral, percutaneous or parenteral administration. Suitable carriers include water, gelatin, gum arabic, lactose, starch, magnesium stearate, talc, vegetable oils, polyalkylene-glycols, petroleum jelly and the like. Furthermore, the pharmaceutical preparations may contain other pharmaceutically active agents. Additional additives such as flavoring agents, stabilizers, emulsifying agents, buffers and the like may be added in accordance with accepted practices of pharmaceutical compounding.

The present invention also pertains to the labeled ligand, compounds, methods, process, uses and composition substantially as hereinbefore described, especially with reference to the following examples.

General Synthesis Schemes

Fluorescent Labeling

In general, the covalent labeling of a cystein containing peptide with maleimide conjugated fluorophore can be accomplished as described below.

A thiol-containing peptide is dissolved in 9:1 DMSO: 50 mM phosphate buffer pH 6 to a final concentration of 1–10 mM. Fluorophore reagent (10–50 mM freshly prepared solution in DMSO) is added stepwise and the mixture left to react at room temperature for a bout 10 minutes. The progress of the reaction is followed by analysis of samples, for example with RP-HPLC. Upon completion, the fluorescent labeled peptide is isolated, for example by RP-HPLC.

Coupling of Cysteine to C-Terminus of Peptide

This synthetic coupling procedure is a standard procedure of peptide synthesis and is known to those skilled in the art. One such procedure that may be used is provided in Chan and White, Fmoc Solid Phase Peptide Synthesis: A Practical Approach (Oxford University Press 2000).

EXAMPLES

The following examples are provided for illustrative purposes and are not intended to limit the scope of applicants' invention.

Example 1

Synthesis of the Labeled Peptides

Example 1.1

Synthesis of 1Gly-Ser-Ser(octanoyl)-Phe-5Leu-Ser-Pro-Glu-His-10Gln-Arg-Val-Gln-Gln-15Arg-Lys-Glu-Ser-Cys-NH$_2$ ((SEQ ID NO: 2)-Cys-NH$_2$, wherein the serine at residue 3 is octanoylated)

Continuous-flow solid-phase synthesis was performed on a Pioneer™ Peptide Synthesis System, starting from Tenta Gel S RAM resin (0.25 mmol/g (Rapp Polymere GmbH, Tübingen, Germany) according to the method described by Chan and White, Fmoc Solid Phase Peptide Synthesis: A Practical Approach, pp. 41–74 (Oxford University Press 2000). The base-labile Fmoc group (Sygena) was used for alpha-amino protection. Side chains were protected with the following protection groups: -Asn(Trt), Glu(OtBu), Ser (tBu), His(Trt), Gln(Trt), His(Trt), Arg(Pbf), Lys(Boc), Cys (Trt). Fmoc-amino acids (4 equiv., Novabiochem) were activated with an equivalent amount of O-(1,2-dihydro-2-oxopyrid-1-yl)-N,N,N',N'-tetramethyluronium tetrafluoroborate (TPTU, Fluka) and N,N-diisopropylethylamine (Hünig's base, Acros). Fmoc deprotection was achieved with 20% piperidine (Fluka) in DMF (Fluka). The automated synthesis was interrupted after residue $^4$Phe was incorporated in the target sequence. Peptide synthesis was continued semi-manually using a Peptide Synthesizer SP650 (Labortec AG). Side chain unprotected Fmoc-$^3$Ser-OH (0.65 g, 2 mmol, Fluka), TPTU (0.59 g, 2 mmol), Hünig's base (1.03 ml) were added to the peptide resin and coupling was continued for 1 hour in DMF solvent (ninhydrin negative). Octanoylation of the side chain hydroxyl was achieved using caprylic acid (2.0 ml, 12 mmol, Fluka), N,N'-Diisopropylcarbodiimide, (1.9 ml, 12 mmol, Fluka) N,N'-dimethylaminopyridine (18 mg, 0.15 mmol, Fluka) in N-methylpyrrolidone (Fluka) solvent. After 4 hours the reaction mixture was filtered off and synthesis was continued using the standard peptide synthesis protocol (above). 1Gly-Ser(tBu)-Ser(octanoyl)-Phe-5Leu-Ser(tBu)-Pro-Glu(OtBu)-His(Trt)-$^{10}$Gln (Trt)-Arg(Pbf)-Val-Gln(Trt)-Gln(Trt)-15Arg(Pbf)-Lys(Boc)-Glu(OtBu)-Ser(tBu)-Cys(Trt)-NH$_2$ ((SEQ ID NO: 2)-Cys-NH2, wherein the serine at residue 3 is octanoylated Tenta Gel S-resin (2.0 g) was treated with a mixture (100 ml) of 95% TFA, 2.5% H$_2$0, 2.5% EDT, 2.5% triisopropylsilane for 5 hours. The reaction mixture was concentrated and poured into diethyl ether and the precipitate was collected by filtration and lyophilized from water. The crude peptide (0.80 g) was purified by preparative RP-HPLC. There was obtained $^1$Gly-Ser-Ser(octanoyl )-Phe-5Leu-Ser-Pro-Glu-His-$^{10}$Gln-Arg-Val-Gln-Gln-$^{15}$Arg-Lys-Glu-Ser-Cys-NH$_2$ ((SEQ ID NO: 2)-Cys-NH$_2$, wherein the serine at residue 3 is octanoylated) (0.18 g, Ion-spray MS analysis $(M+2H)^{2+}/2=1165.4$, $(M+3H)^{3+}/3=777.2$).

Example 1.1b

Synthesis of 1Gly-Ser-Dapa(N-octanoyl)-Phe-5Leu-Ser-Pro-Glu-His-10Gln-Arg-Val-Gln-Gln-$^{15}$Arg-Lys-Glu-Ser-Cys-NH$_2$ ((SEQ ID NO: 2)-Cys-NH$_2$ wherein the serine at residue 3 is substituted with Dapa(N-octanoyl)

(S)-2-(9H-Fluoren-9-ylmethoxycarbonylamino)-3-octanoylamino-propionic acid Fmoc-L-Dapa(N-octanoyl)-OH To a pre-activated mixture containing caprylic acid (1.54 ml, 10 mmol), TPTU (2.8 g, 9.5 mmol) and Hunig's base (3.4 ml, 20 mmol )) in DMF (20 ml) was added a solution of Fmoc-L-Dapa-OH Neosysytem FA04002 8 (3.3 g, 10 mmol) in DMF (10 ml). The reaction mixture was stirred for 1 h, concentrated under reduced pressure dissolved in ethyl acetate and washed with 5%/10% KHSO$_4$/K$_2$SO$_4$, brine, dried over Na$_2$SO$_4$, filtered and concentrated. Crystallizaton from ethyl acetate/hexane: 3.7 g, 82%; MS=451.4 (MH)$^-$.

The peptide synthesis incorporating Fmoc-L-Dapa(N-octanoyl)-OH was performed on a Pioneer™ Peptide Synthesis System as described above starting with Tentagel S-NH2 resin (0.55 mmol), yielding purified peptide 1Gly-Ser-Dapa (N-octanoyl)-Phe-5Leu-Ser-Pro-Glu-His-$^{10}$Gln-Arg-Val-Gln-Gln-$^{15}$Arg-Lys-Glu-Ser-Cys-NH$_2$ ((SEQ ID NO:

2)-Cys-NH$_2$, wherein the serine at residue 3 is substituted with Dapa(N-octanoyl)): 135 mg; Ion-spray MS: (M+2H)$^{2+}$/2=1164.8, (M+3H)$^{3+}$/3=776.8).

Conjugation of Peptides to Fluorophores

Example 1.2

$_1$Gly-Ser-Ser(octanoyl)-Phe-$^5$Leu-Ser-Pro-Glu-His-
$_{10}$Gln-Arg-Val-Gln-Gln-$^{15}$Arg-Lys-Glu-Ser-Cys
(TxR)-NH$_2$ ((SEQ ID NO: 2)-Cys-F, wherein the
serine at residue 3 is octanoylated The thiol-containing peptide above (1.3 mg) was dissolved in 9:1 DMSO: 50 mM phosphatebuffer pH 6 to a final concentration of 2.5 mM. 1.2 equivalent of TxR (Texas Red)-Maleimide (30 mM freshly prepared solution in DMSO, from Molecular Probes, Leiden, Netherlands, Product No. #T-6008) was added and the mixture left to react at room temperature for 10 minutes. The reaction mixture was directly purified by RP-HPLC: 0.17 mg. MS analysis: calculated monoisotopic mass: C136H198N36O39S3=3055.38; found monoisotopic mass: 3055.35

Example 1.3

$_1$Gly-Ser-Ser(octanoyl)-Phe-$^5$Leu-Ser-Pro-Glu-His-
$_{10}$Gln-Arg-Val-Gln-Gln-$^{15}$Arg-Lys-Glu-Ser-Cys
(TMR)-NH$_2$ ((SEQ ID NO: 2)-Cys-F, wherein the
serine at residue 3 is octanoylated)

The TMR (Tetramethylrhodamine) derivatized peptide (Molecular Probes, Leiden, Netherlands, Product No. #T-6027) was prepared analogously to example 1.2: From 1.7 mg starting peptide material was isolated 0.44 mg labeled peptide. MS analysis: calculated monoisotopic mass: C127H185N35O36S=2808.34; found monoisotopic mass: 2808.40

Example 1.4

$_1$Gly-Ser-Ser(octanoyl)-Phe-$^5$Leu-Ser-Pro-Glu-His-
$_{10}$Gln-Arg-Val-Gln-Gln-$^{15}$Arg-Lys-Glu-Ser-Cys
(MR121)-NH$_2$ ((SEQ ID NO: 2)-Cys-F, wherein
the serine at residue 3 is octanoylated)

The MR121* derivatized peptide was prepared analogously to example 2: From 1.5 mg initial peptide material was isolated 0.37 mg labeled peptide. MS analysis: calculated monoisotopic mass: C129H196N37O35S=2855.44; found monoisotopic mass: 2855.38

*MR-121 is an oxazine fluorescent dye. [see lit.: "New fluorescent dyes in the red region for biodiagnostics" M. Sauer et al 1995 J. Fluoresc. Vol. 5, pp 247–261]; Reference for MR121: Marmé et al., Bioconjugate Chem. 2003, 14, 1133–1139.

Example 1.5

$_1$Gly-Ser-Ser(octanoyl)-Phe-$^5$Leu-Ser-Pro-Glu-His-
$_{10}$Gln-Arg-Val-Gln-Gln-$^{15}$Arg-Lys-Glu-Ser-Cys(BO-
DIPY-FL)-NH$_2$ ((SEQ ID NO: 2)-Cys-F, wherein
the serine at residue 3 is octanoylated)

The BODIPY-FL (4,4-difluoro-5,7-dimethyl-4-bora-3a, 4a-diaza-s-indacene-3-propionic acid, from Molecular Probes, Leiden, Netherlands, Product No. #B-10250) derivatized peptide was prepared analogously to example 2: From 0.7 mg starting material was isolated 0.20 mg labeled peptide. MS analysis calculated monoisotopic mass: C119H183BF2N36O34S=2742.4; found monoisotopic mass: 2742.4.

Example 1.6

$_1$Gly-Ser-Dapa(N-octanoyl)-Phe-$^5$Leu-Ser-Pro-Glu-
His-$_{10}$Gln-Arg-Val-Gln-Gln-$^{15}$Arg-Lys-Glu-Ser-Cys
(MR121)-NH$_2$ ((SEQ ID NO: 2)-Cys-F, wherein
the serine at residue 3 is substituted with Dapa(N-
octanoyl)

The MR121* derivatized peptide was prepared analogously to example 2: From 0.7 mg initial peptide material was isolated 0.17 mg labeled peptide. MS analysis: calculated monoisotopic mass: C129H197N36O35S=2854.46; found monoisotopic mass: 2854.49.

*MR-121 is an oxazine fluorescent dye. [see lit.: "New fluorescent dyes in the red region for biodiagnostics" M. Sauer et al 1995 J. Fluoresc. Vol. 5, pp 247–261]; Reference for MR121: Marmé et al., Bioconjugate Chem. 2003, 14, 1133–1139.

Example 2

Binding Assay

Example 2.1

Membrane Preparation

Human Embryonic Kidney HEK 293 (EBNA) cells were grown in suspension and transfected according to the method previously described (Schlaeger and Christensen, Cytotechnology, 30, 71–83, 1999). The cells were centrifugated for 10 min at 500 rpm, washed once with PBS-0.7 mM EDTA/(4° C.) and resuspended in PBS-EDTA-PI (with Protease inhibitor cocktail), at 2 ml/g of cells. Cells were broken with Ultra Turax level green 3×15" with 30" breaks on ice. To remove debris the suspension was centrifugated in a Sorvall SS34 rotor for 20 min at 2000 rpm. The supernatant was collected and centrifugated for 40 min at 20'000 rpm. The pellet was resuspended in PBS-EDTA. Receptor density was verified with saturation binding assay using T-MK 0677 to be 4.9 pmol/mg protein.

Example 2.2

FP-Assay

Example 2.2.1

Assay Development

GHSR-1a-containing cell-membranes was diluted in FP-buffer: 25 mM Hepes, 5 mM MgCl$_2$, 1 mM CaCl$_2$, 4% PEG, 0.1% BSA (fraction V) to a to a final volume of 0.5–1 ml, passed through a 0.4 mm syringe and sonicated 4 times 20 pulses while kept on ice. 10 nM solution of MR121-labeled ghrelin (tracer) and 20× concentrated solutions of competitor in FP-buffer were prepared. To determine polarization of receptor bound tracer, three samples of 180 ul were prepared: Total bound: Membranes+tracer, Free ligand: membranes+tracer+competitor, Fluorescence background: membranes+buffer. 3×50 µl of each sample was transferred to assay-plates right after mixing.

Example 2.2.2

HTS Protocol for FP-Ghrelin Competition Binding Assay

FIG. 1. shows a possible layout of a 384 well plate for High Throughput Screening.

For one round of screening, 119 Sample Plates and 1 DMSO Plate (membranes p20F1+p22F1) were used. The following is a representative non-limiting example of a HTS protocol with MR121 as fluorochrome. For the assay, Costar 384 well UV plates with non-binding surface were used. The following assay buffer was used: 25 mM Hepes pH 7.2, 5 mM $MgCl_2$, 1 mM $CaCl_2$, 4% polyethylene glycol, and 0.1% BSA (Fract. V) was added fresh every week. Receptors were provided as follows: Membranes were isolated as described in example 2.1. Final assay concentration was 1.4 nM of GHSR-1a as determined by 125 I-ghrelin saturation binding. Typical values for the membrane stock are: Bmax=6 fmol/µg; Protein Concentration=50 µg/µl.

To avoid sedimentation membranes need to be pushed through a needle (3×/0.4 mm) and sonicated "Branson sonifier 250" set to intensity level 3–4, 4×20 pulses separated by 30 sec pause. Membranes were kept on ice during sonication. Membranes were diluted to an endconcentration of 1.4 nM of receptor.

The tracer ghrelin(1–19) [K19MR121] was diluted in buffer from 1 µM DMSO stock. Final assay concentration was 0.5 nM. Since the peptide tends to adsorb to surfaces, the plastic ware used for the diluted peptide solution either comprised a nonbinding surface or was blocked overnight with a 1% casein solution, and then washed with buffer before use.

The following steps were used for high throughput screening:

1) 30 µl of 1.33× membrane solution were added to all wells of the assay plate.
2) 4.4 µl of buffer were transferred to "FPBLK"/"100% control" wells and 4.4 µl of reference compound solution were transferred to "STD" and "0% control" wells from a reservoir plate to the assay plate
3) 10 µl of water with 0% DMSO were added to columns 3 to 24 of the compound storage plate containing 1 µl of 2 mM compounds (Endconc. 20 µM).
4) The contents of the storage plate were mixed.
5) 4.4 µl of diluted compounds were transferred from the storage plate to an assay plate.
6) The contents of the assay plate were mixed five times and then incubated for 30 min at 24° C.
7) 5.6 µl of 7.143× tracer solution were added to the assay plate except to wells A1 to D2 (wells labeled "FPBLK" in FIG. 1) to which 5.6 µl of buffer were added.
8) The content of the assay plate was mixed five times.
9) 30 µl of the solution in each well were transferred from the assay plate to the read-out plate (Corning UV non-binding surface).
10) The readout plate was incubated for 10 min. at RT.
11) MR121 fluorescence was read from the read-out plate at 650-695 nm (5 s, Focus To Bottom 1 mm, xy scan 0.5 mm), with settings at parallel (∥) and crossed (⊥) polarization, using a Zeiss plate::vision microtiter plate reader.

---

The invention claimed is:

1. A method of identifying a cellular receptor as a growth hormone secretagogue receptor comprising (a) contacting a host suspected to express a growth hormone secretagogue receptor with a labeled growth hormone secretagogue of the formula R1-Cys-F wherein R1 is SEQ ID NO. 2, wherein the serine residue three may be octanoylated or substituted with Dapa(N-octanoyl), and F is a fluorochrome; and (b) determining whether binding has occurred.

2. A method for identifying a compound that can bind to a growth hormone secretagogue receptor comprising a) contacting said compound with a membrane isolated from a host expressing a growth hormone secretagogue receptor in the presence of the labeled growth hormone secretagogue of the formula R1-Cys-F wherein R1 is SEQ ID NO. 2, wherein the serine residue three may be octanoylated or substituted with Dapa(N-octanoyl), and F is a fluorochrome, in an assay buffer; b) washing said membrane to remove unbound labeled growth hormone secretagogue; and c) monitoring whether the compound influences the binding of said labeled growth hormone secretagogue to the growth hormone secretagogue receptor by measuring the fluorescence of said membranes.

3. The method of claim 2, wherein said method is a high throughput screening method.

4. The method of claim 2, wherein said assay buffer has a pH of 7.2.

5. A method for identifying a compound that has growth hormone secretagogue activity comprising (a) contacting the test compound with a host expressing a growth hormone secretagogue receptor in the presence of the labeled growth hormone secretagogue of formula R1-Cys-F wherein R1 is SEQ ID NO. 2, wherein the serine residue three may be octanoylated or substituted with Dapa(N-octanoyl), and F is a fluorochrome; and (b) determining whether the test compound influences the binding of said labeled growth hormone secretagogue of claim 1 to the growth hormone secretagogue receptor.

* * * * *